(12) United States Patent
Zheng et al.

(10) Patent No.: US 10,131,619 B2
(45) Date of Patent: Nov. 20, 2018

(54) α-ASARY-LALDEHYDE ESTER, PREPARATION METHOD THEREFOR, AND APPLICATION THEREOF

(71) Applicant: NORTHWEST UNIVERSITY, Xi'an, Shaanxi (CN)

(72) Inventors: Xiaohui Zheng, Shaanxi (CN); Fanggang Qin, Shaanxi (CN); Yajun Bai, Shaanxi (CN); Shixiang Wang, Shaanxi (CN); Yi Zhang, Shaanxi (CN); Xirui He, Shaanxi (CN); Pei Liu, Shaanxi (CN)

(73) Assignee: NORTHWEST UNIVERSITY, Xi-An, Shaanxi (CN)

( * ) Notice: Subject to any disclaimer, the term of this patent is extended or adjusted under 35 U.S.C. 154(b) by 0 days.

(21) Appl. No.: 15/529,283

(22) PCT Filed: Nov. 26, 2015

(86) PCT No.: PCT/CN2015/095686
§ 371 (c)(1),
(2) Date: May 24, 2017

(87) PCT Pub. No.: WO2016/082780
PCT Pub. Date: Jun. 2, 2016

(65) Prior Publication Data
US 2017/0260122 A1    Sep. 14, 2017

(30) Foreign Application Priority Data
Nov. 26, 2014  (CN) .......................... 2014 1 0699506

(51) Int. Cl.
C07C 69/00 (2006.01)
C07C 69/78 (2006.01)
C07C 69/734 (2006.01)
C07C 69/732 (2006.01)
C07C 69/33 (2006.01)
C07C 67/08 (2006.01)
C07D 213/80 (2006.01)
C07D 207/16 (2006.01)

(52) U.S. Cl.
CPC .............. *C07C 69/78* (2013.01); *C07C 67/08* (2013.01); *C07C 69/33* (2013.01); *C07C 69/732* (2013.01); *C07C 69/734* (2013.01); *C07D 207/16* (2013.01); *C07D 213/80* (2013.01); *A61K 2121/00* (2013.01)

(58) Field of Classification Search
CPC ....... C07C 69/33; C07C 69/732; C07C 69/78; A61K 2121/00
See application file for complete search history.

(56) References Cited

FOREIGN PATENT DOCUMENTS

| CN | 101015543 A | 8/2007 |
|----|-------------|--------|
| CN | 101215226 A | 7/2008 |
| CN | 101974011 A | 2/2011 |
| CN | 102648937 A | 8/2012 |
| CN | 104529724 A | 4/2015 |
| CN | 104529775 A | 4/2015 |

OTHER PUBLICATIONS

International Search Report correpsonding to Application No. PCT/CN2015/095686; dated Feb. 29, 2016.
J. Wang etal., "Pd(II)-catalyzed decarboxylative allylation and Heck-coupling of arene carboxylates with allylic halides and esters," Organic & Biomolecular Chemistry; 2011, pp. 663-666, vol. 9.
Notification of Reasons for Refusal for corresponding JP Application No. 2017-527866; dated Apr. 24, 2018.
Benjamin D. Dickson et al., "Synthesis of 2,3-syn-diarylpent-4-enamides via acyl-Claisen rearrangements of substituted cinnamyl morpholines: application to the synthese of magnosalicin," SciVerse ScienceDirect, 2012, pp. 4464-4468.
Extended European Search Report corresponding to Application No. 15863145.7-1109/3225616 PCT/CN2015095686; dated Jun. 8, 2018.
F. Zhang et al., "Qualitative and quantitative analysis of the major constituents in Acorus tatarinowii Schott by HPLC/ESI-QTOF-MS/MS," Biomedial Chromatography; Oct. 30, 2014, pp. 890-901.

*Primary Examiner* — Ana Z Muresan
(74) *Attorney, Agent, or Firm* — Cantor Colburn LLP

(57) ABSTRACT

The present invention relates to α-asary-laldehyde ester. The chemical structure of the related α-asary-laldehyde ester is of formula I.

2 Claims, No Drawings

α-ASARY-LALDEHYDE ESTER, PREPARATION METHOD THEREFOR, AND APPLICATION THEREOF

The present application is a U.S. national stage of application No. PCT/CN2015/095686, filed Nov. 26, 2015 which claims priority under 35 U.S.C. § 119(a) and 35 U.S.C. § 365(b) of Chinese Application No. 201410699506.6, as filed on Nov. 26, 2014, and titled with "α-asary-laldehyde ester, preparation method therefor, and application thereof", and the disclosure of which is also incorporated herein by reference.

FIELD

The present invention mainly relates a method for preparing ester of α-Asaronol (3-(2,4,5-Trimethoxy-phenyl)-prop-2-en-1-ol) and drug research for calming, mind tranquillizing, senile dementia resisting, convulsion resisting, epilepsy resisting and depression resisting.

BACKGROUND

Acorns gramineus soland is first recorded in the "Shen Nong's Herbal Classic" as top grade and is derived from the dried rhizome of araceae perennial herb, *Acorus tatarinowii* schott. Acorns gramineus soland has warm property, pungent and bitter taste and aromatic odor, and can entry the heart and stomach meridian. Acorns gramineus soland has aromatic smell, pungent taste and warm property, can remove dampness to restore normal functioning of the stomach and dissipate phlegm for resuscitation, and has the effect of promoting the intelligence and tranquilizing the mind, and thus is commonly used for treatment of stroke, phlegm syncope epilepsy, coma, forgetfulness and so on. The main chemical composition comprises volatile oil mainly containing β-asarone, α-asarone and the like, amino acids and sugars, etc. Modern pharmacological studies suggest that Acorus gramineus soland has anti-dementia, nerve cell protection, anti-mutation, antiepileptic effects and so on.

*Polygala tenuifolia* is first recorded in the "Shen Nong's Herbal Classic" as top grade and derived from the dried root of polygalaceae *polygala tenuifalia* Willd. or *polygala sibirica* L. *Polygala tenuifolia* has bitter and pungent taste and warm property, and has the effect of promoting the intelligence and tranquilizing the mind, as well as eliminating phlegm and diminishing swelling. The chemical composition of *polygala tenuifolia* mainly comprises triterpenoid saponins, sugar esters and xanthones, and also contains a small amount of alkaloids, coumarin, lignin and so on. Studies have shown that *Polygala tenuifolia* has good activity in dementia resisting, brain protection, sedation, convulsion resisting, depression resisting, expectorant and antitussive, cardiovascular and cerebrovascular protection, etc.

Wang Shasha et al. found, in the blood and bile of rats intragastrically administrated with extract of *Polygala tenuifolia*, active substances 3,4,5-trimethoxycinnamic acid (TMCA), methyl 3,4,5-trimethoxycinnamic acid (M-TMCA) and p-methoxycinnamic acid (PMCA) which can prolong the time of pentobarbital sodium-induced sleep in mice, suggesting the water extract of Polygala tenuifolia contains natural prodrugs of TMCA (WANG S. S. WaKan Iyakugaku Zasshi, 1995, 12(2), 102).

LING Yangzhi et al. performed structural combination of TMCA and obtained 3,4,5-trimethoxy cinnamamide compounds, which have good anticonvulsant activity (LING Yangzhi, Pharmaceutical Industry, 1987, 18 (2): 56).

Based on the good pharmacological activity of TMCA from *Polygala tenuifolia* and α-asarone from *Acorns gramineus* soland in calming, mind tranquillizing, convulsion resisting and nerve cell protection, we designed 3,4,5-trimethoxycinnamate α-Asaronol ester and a series of ester derivatives of α-Asaronol by structural and pharmacophore combination, hoping to obtain new chemical drugs with more effectiveness in senile dementia resisting, brain protection, calming, convulsion resisting, depression resisting and the like.

SUMMARY

The present invention provides an ester of α-Asaronol, having the structure represented by formula I

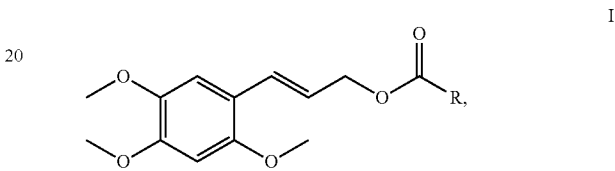

wherein,
R is a branched or linear $C_{1-12}$ alkyl, alkenyl or alkynyl; a $C_{3-9}$ cycloalkyl or substituted cycloalkyl; a $C_{3-9}$ cycloalkenyl or substituted cycloalkenyl; an aryl, a monosubstituted aryl or a polysubstituted aryl; a heterocyclic aryl, a monosubstituted heterocyclic aryl or a polysubstituted heterocyclic aryl; or an amino acid group.

Further optionally, the R is an arylmethyl, a monosubstituted arylmethyl or a polysubstituted arylmethyl; an arylethyl, a monosubstituted or polysubstituted arylethyl; an arylvinyl, a monosubstituted or polysubstituted arylvinyl; or a substituted phenoxyethyl.

Further optionally, the R is:

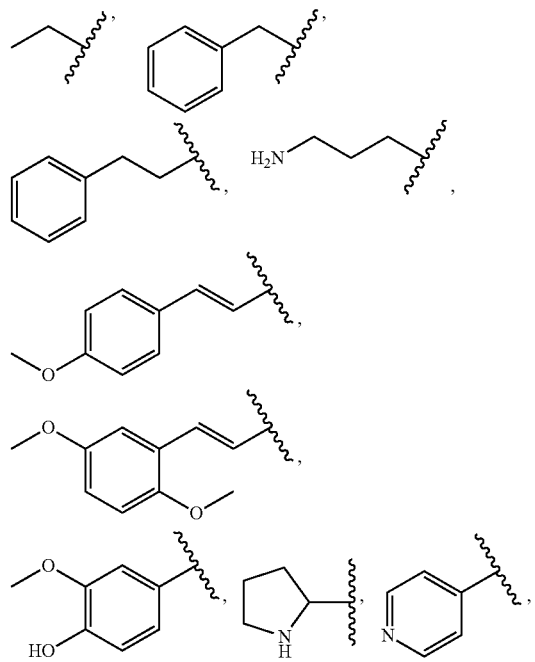

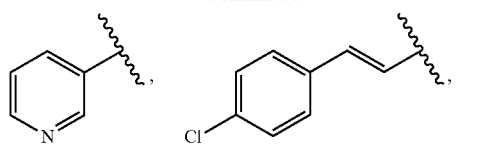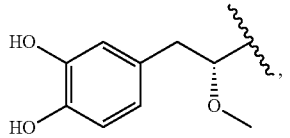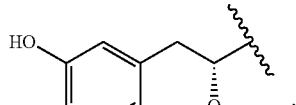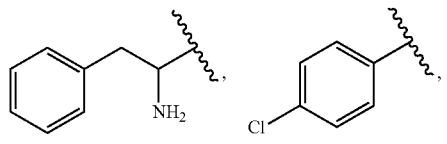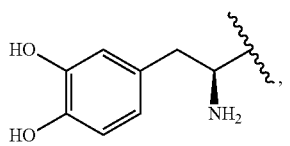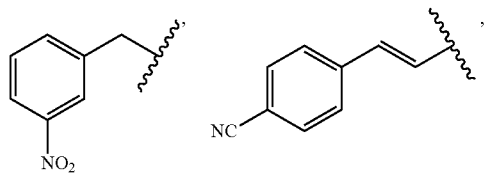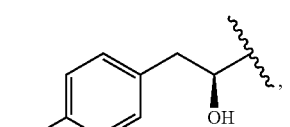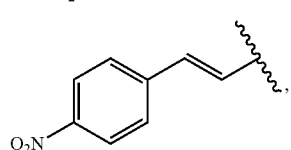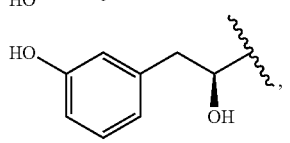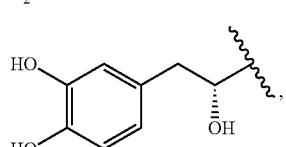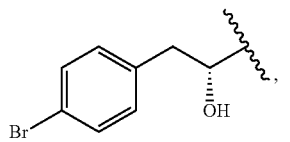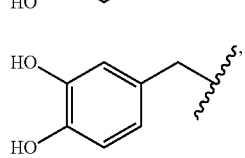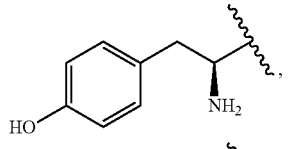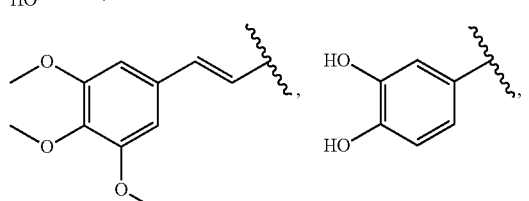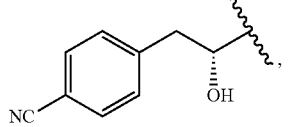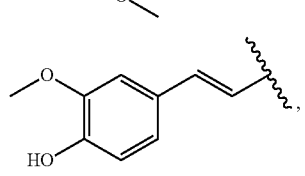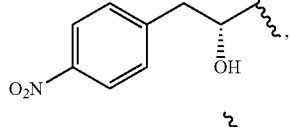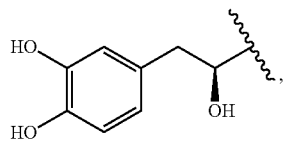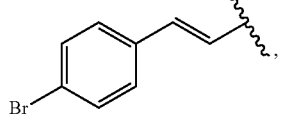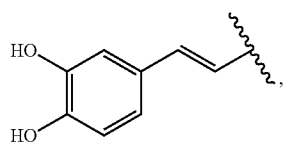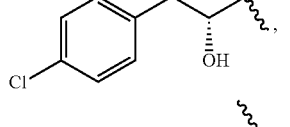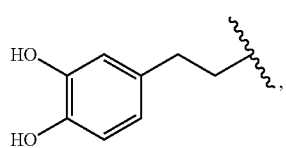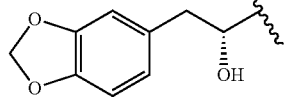 or

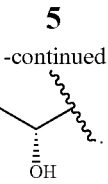

The present invention also provides a method for preparing the ester of α-Asaronol above, comprising: sequentially adding the compound of formula II, the compound of formula III and the catalyst in a molar ratio of 1.0 to 2.0:1.0 to 2.0:0.1 to 1.0 into a reaction vessel containing a suitable organic solvent, and after complete dissolution, adding a dehydrating agent, wherein the molar ratio of the dehydrating agent to the compound of formula II is 1 to 2:1, stirring the mixture at room temperature for 5-20 hours, and after completion of the reaction, extracting the reaction mixture with ethyl acetate/water to separate the organic phase, which is then dried over anhydrous sodium sulfate, concentrated, and purified by column chromatography to obtain the product,

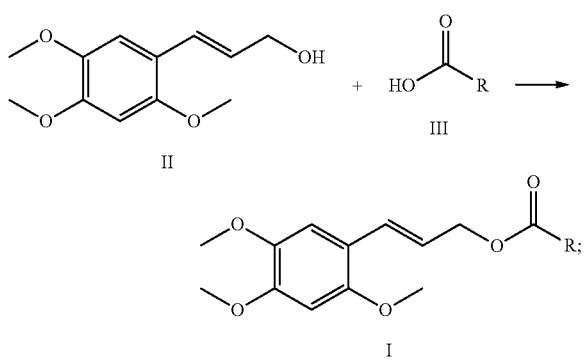

wherein the catalyst is one of pyridine, 2,4,6-trimethylpyridine, 2,6-dimethylpyridine, 2,6-di-tert-butyl-4-methylpyridine and 4-dimethylpyridine(DMAP), or any combination thereof;
the organic solvent is one of dichloromethane, trichloromethane, tetrachloromethane, tetrahydrofuran, ethyl acetate, methyl tert-butyl ether, diethyl ether, 1,4-dioxane, N,N-dimethylformamide, N-methyl pyrrolidone, N,N-dimethylacetamide and dimethylsulfoxide, or any combination thereof; and
the dehydrating agent is dicyclohexylcarbodiimide (DDC), 1-(3-dimethylaminopropyl)-3-ethylcarbodiimide hydrochloride(EDCI), or diisopropylcarbodiimide (DIC).

The present invention also provides another method for preparing the ester of α-Asaronol above, comprising:
reacting α-Asaronol with the compound of formula III under the Mitsunobu reaction condition to obtain ester of α-Asaronol

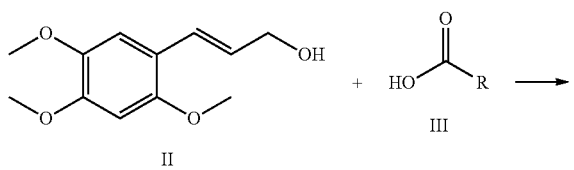

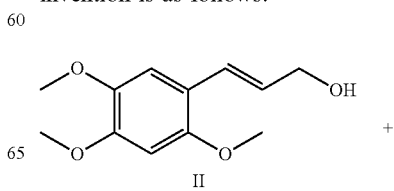

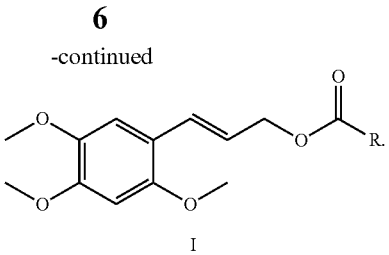

Specifically, the method comprises dissolving α-Asaronol, the compound of formula III, an azo compound, and an organophosphorus compound in a molar ratio of 1 to 1.5:1 to 1.5:1 to 1.5:1 to 1.5 in dry tetrahydrofuran, reacting at room temperature for 10-48 hours, extracting the reaction mixture with ethyl acetate/water to separate the organic phase, which is then dried over anhydrous sodium sulfate, concentrated, and purified by column chromatography to obtain the product.

Optionally, the azo compound is diethyl azodicarboxylate (DEAD), diisopropyl azodicarboxylate(DIAD), azodicarboxylic dipiperidide(ADDP), N,N,N',N'-tetramethylazodicarboxamide(TMAD), N,N,N',N'-tetraisopropylazodicarboxamide(TIPA) or 4,7-dimethyl-3,4,5,6,7,8-hexahydro-1,2,4,7-tetraazadicin-3,8-dione(DHTD).

Optionally, the organophosphorus compound is triphenylphosphine, tributylphosphine or trimethylphosphine.

The present also provides a stereoisomer or a mixture of different stereoisomeric compounds of the compound above.

The present also provides use of the compound above in the preparation of medicament for calming, mind tranquillizing, senile dementia resisting, convulsion resisting, epilepsy resisting and depression resisting.

DESCRIPTION

The present invention provides an ester of α-Asaronol, having the structure represented by formula I

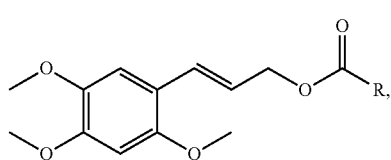

wherein, in formula I, R is a branched or linear $C_{1-12}$ alkyl, alkenyl or alkynyl; a $C_{3-9}$ cycloalkyl or substituted cycloalkyl; a $C_{3-9}$ cycloalkenyl or substituted cycloalkenyl; an aryl, a monosubstituted or polysubstituted aryl; a heterocyclic aryl, a monosubstituted heterocyclic aryl or a polysubstituted heterocyclic aryl; an arylmethyl, a monosubstituted arylmethyl or a polysubstituted arylmethyl; an arylethyl, a monosubstituted or polysubstituted arylethyl; an arylvinyl, a monosubstituted or polysubstituted arylvinyl; a substituted phenoxyethyl; or an amino acid group.

A method for preparing the compound of the present invention is as follows:

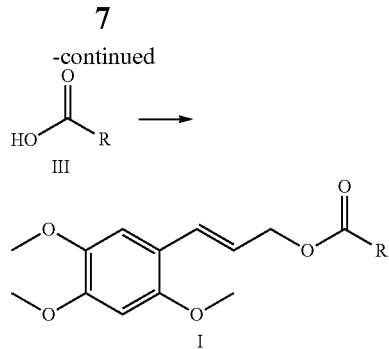

optionally, scheme (1): reacting the compound of formula II with the compound of formula III in the presence of a dehydrating agent/catalyst to obtain the corresponding ester of α-Asaronol (the compound of formula I); wherein sequentially adding the compound of formula II, the compound of formula III and the catalyst in a molar ratio of 1.0 to 2.0:1.0 to 2.0:0.1 to 1.0 into a reaction vessel containing a suitable organic solvent, and after complete dissolution, adding a dehydrating agent, wherein the molar ratio of the dehydrating agent to the compound of formula II is 1 to 2:1, stirring the mixture at room temperature for 5-20 hours, and after completion of the reaction, extracting the reaction mixture with ethyl acetate/water to separate the organic phase, which is then dried over anhydrous sodium sulfate, concentrated, and purified by column chromatography to obtain the product. In the scheme, the molar ratio of the compound of formula II, the compound of formula III and the catalyst is preferably 1.0:1.0 to 1.2:0.1 to 0.3.

In the scheme, the catalyst comprises pyridine, 2,4,6-trimethylpyridine, 2,6-dimethylpyridine, 2,6-di-tert-butyl-4-methylpyridine, 4-dimethylpyridine, or any combination thereof, and preferably, 4-dimethylpyridine is used as the catalyst;

the organic solvent comprises dichloromethane, trichloromethane, tetrachloromethane, tetrahydrofuran, ethyl acetate, methyl tert-butyl ether, diethyl ether, 1,4-dioxane, N,N-dimethylformamide, N-methyl pyrrolidone, N,N-dimethylacetamide, dimethylsulfoxide, or any combination thereof, and preferably, N,N-dimethylformamide, dichloromethane or tetrachloromethane is used as the solvent; and the dehydrating agent is dicyclohexylcarbodiimide (DDC), 1-(3-dimethylaminopropyl)-3-ethylcarbodiimide hydrochloride(EDCI), or diisopropylcarbodiimide (DIC), and preferably, EDCI is used as the dehydrating agent.

Optionally, scheme (2): producing an acid chloride compound from the compound of formula III and then reacting the acid chloride compound with the compound of formula II to obtain the corresponding ester of α-Asaronol (the compound of formula I), particularly as follows: adding thionyl chloride into the compound of formula III in ice bath, refluxing the mixture for 2-5 hours, coolling, and distilling under reduced pressure to remove excess thionyl chloride; adding tetrahydrofuran into the residue with stirring to obtain the solution of the compound of formula III in acid chloride-tetrahydrofuran; adding the solution of the compound of formula III in acid chloride-tetrahydrofuran above into a tetrahydrofuran solution comprising the compound of formula II and pyridine in ice bath and stirring for 10-20 min and then heating to reflux for 3-4 hours; after the completion of the reaction, cooling and filtering the reaction mixture to remove pyridine hydrochloride; distilling tetrahydrofuran off from the filtrate under reduced pressure, and extracting with ethyl acetate/water to separate the organic phase, which is then dried over anhydrous sodium sulfate, concentrated, and purified by column chromatography to obtain the product.

In the scheme, the molar ratio of the compound of formula III to thionyl chloride is from 1:10 to 1:100, preferably the molar ratio of the compound of formula III to the thionyl chloride is 1:50.

Optionally, scheme (3): reacting the compound of formula II with the compound of formula III under the Mitsunobu reaction condition to obtain the compound of formula I, particularly as follows:

dissolving the compound of formula II, the compound of formula III, an azo compound, and an organophosphorus compound in a molar ratio of 1 to 1.5:1 to 1.5:1 to 1.5:1 to 1.5 in dry tetrahydrofuran, reacting at room temperature for 10-48 hours, extracting the reaction mixture with ethyl acetate/water to separate the organic phase, which is then dried over anhydrous sodium sulfate, concentrated, and purified by column chromatography to obtain the product, wherein preferably, the molar ratio of the compound of formula II, the compound of formula III, the azo compound, and the organophosphorus compound is 1:1 to 1.1:1 to 1.2:1 to 1.2.

In the scheme, the azo compound comprises diethyl azodicarboxylate (DEAD), diisopropyl azodicarboxylate (DIAD), azodicarboxylic dipiperidide(ADDP), N,N,N',N'-tetramethyl azodicarboxamide(TMAD), N,N,N',N'-tetraisopropylazodicarboxamide(TIPA) or 4,7-dimethyl-3,4,5,6,7,8-hexahydro-1,2,4,7-tetraazadicin-3,8-dione(DHTD), and preferably DIAD and DEAD.

The organophosphorus compound comprises triphenylphosphine, tributylphosphine or trimethylphosphine, and preferably triphenylphosphine. The compound of formula I of the present invention can comprise one or more asymmetric carbon atoms, and any stereoisomers thereof and mixtures of the stereoisomers are within the scope of the present invention.

Drug research of the compound of formula I for calming, mind tranquillizing, senile dementia resisting, convulsion resisting, epilepsy resisting and depression resisting.

The method for preparing a-Asaronol involved in the present invention comprising:

(1) reacting compound IV with compound V in the presence of a fatty alcohol and a catalyst to give compound VI:

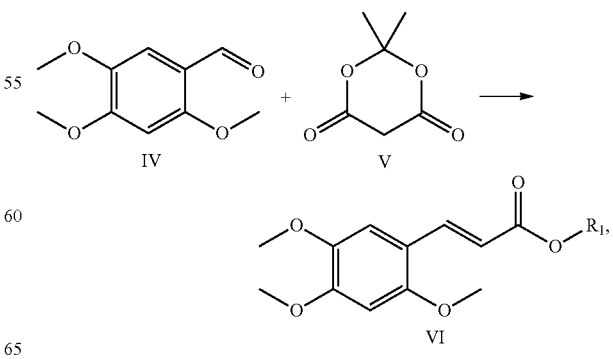

wherein $R_1$ is selected from a linear or branched $C_1$-$C_5$ alkyl;

(2) reducing compound VI to give compound II;

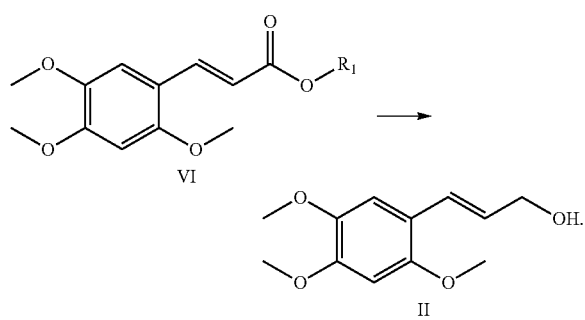

Step (1) is particularly as follows. Compound V and the aliphatic alcohol are first refluxed in xylene, toluene or benzene for 3-12 hours, and preferably for 4-10 hours. After cooling to room temperature, 2,4,5-trimethoxybenzaldehyde (compound IV) and catalyst are added to the reaction mixture, and the mixture is refluxed for 5-24 hours and preferably for 8-14 hours to give compound VI. The aliphatic alcohol used in step (1) is one of methanol, ethanol, propanol, isopropanol, butanol, isobutanol, n-amyl alcohol and isoamyl alcohol, or any combination thereof, and preferably one of methanol and ethanol, or any combination thereof. The molar ratio of the aliphatic alcohol to compound V is 1:1 to 1:10, and preferably the molar ratio of the aliphatic alcohol to compound V is 1:1 to 1:4. The catalyst used is one of pyridine, 2,4,6-trimethylpyridine, 2,6-dimethylpyridine, 2,6-di-tert-butyl-4-methylpyridine, 4-dimethylpyridine, piperidine and tetrahydropyrrole, or any combination thereof. The molar ratio of the catalyst to 2,4,5-trimethoxybenzaldehyde is 0.1:1 to 2:1.

In step 2, the reducing agent used is sodium borohydride, sodium dihydro-bis(2-methoxyethoxy) aluminate, lithium aluminum hydride or diisobutylaluminum hydride, and the molar ratio of the reducing agent to compound VI is 1:1 to 10:1. The solvent used is one of tetrahydrofuran, 1,4-dioxane, dimethylethyl ether, toluene, benzene, xylene, diethyl ether, methyl tert-butyl ether, dichloromethane, dichloroethane, trichloromethane, tetrachloromethane and n-hexane or any combination thereof. The reaction temperature is between −78° C. and 25° C.; and the reaction time is between 0.5 and 24 hours.

The present invention will be better understood from the following description of the examples, which are illustrative only and the advantageous embodiments of the present invention are not limited thereto.

The α-Asaronol used in the following examples was synthesized by the following method.
Preparation of methyl 2,4,5-trimethoxycinnamate Meldrum's acid 195.5 g (1.35 mol), methanol (50 mL) and toluene (750 mL) were added respectively to a 3 L three-necked flask equipped with a thermometer and a condenser tube and heated at 110° C. to reflux for 4 hours. After cooling to room temperature, 2,4,5-trimethoxybenzaldehyde 196.2 g (1.0 mol), pyridine 134.5 g (1.7 mol) and piperidine 14.5 g (0.17 mol) were added into the reaction mixture and heated to reflux for 18 hours. After concentration under reduced pressure, ethyl acetate (200 mL) and water (200 mL) were added to the mixture and the mixture was extracted and seperated three times. The organic phases were combined and concentrated under reduced pressure, and then ethanol (1000 mL) was added. The organic material was placed in a refrigerator overnight and allowed to precipitate. After suction filtration, the residue was washed three times with 500 mL of ice ethanol to obtain 166.3 g of a pale yellow solid with 66% yield.

$LiAlH_4$ 28.5 g (0.75 mol) (dissolved in 250 ml of tetrahydrofuran) was added into a 3 L three-necked flask equipped with a constant pressure funnel and stirred under ice bath for 20 minutes. Into the mixture $AlCl_3$ 42.6 g (0.32 mol) (dissolved in 150 ml of tetrahydrofuran) was added and stirred for 30 minutes, and then methyl 2,4,5-trimethoxycinnamate 63.1 g (0.25 mol) (dissolved in 200 mL of tetrahydrofuran) was slowly added dropwise at 0° C. The mixture was slowly warmed and stirred at room temperature for 1 hour. Then, water (23 g), 10% sodium hydroxide (23 mL) and water (69 mL) were added slowly. After precipitation, the mixture was suction filtered and concentrated under reduced pressure. Then, ethyl acetate (50 mL) and water (100 mL) was added to the mixture and the mixture was extracted and separated three times. The organic phases were combined, dried over anhydrous sodium sulfate, suction filtered, and concentrated under reduced pressure. The resulting crude product was isolated by silica gel column to obtain 28.0 g of a pale yellow solid in 50% yield.

EXAMPLE 1

α-Asaronol 3,4,5-trimethoxycinnamate

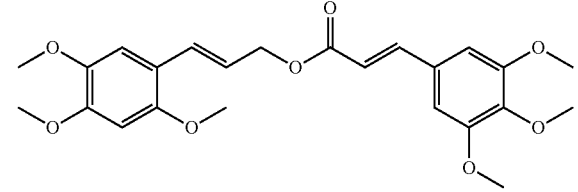

Into a 250 mL single-necked flask, α-Asaronol 11.20 g (50.0 mmol), 3,4,5-trimethoxycinnamic acid 17.85 g (75.0 mmol), DMAP 1.83 g (15.0 mmol) and dichloromethane (120 mL) were added. After stirring the mixture at room temperature for 30 minutes, EDCI 14.38 g (75.0 mmol) was added and reacted at room temperature for 6 hours. The reaction was monitored by TLC. After the completion of the reaction of raw materials, saturated sodium bicarbonate solution was added to adjust the pH to pH=7-8. The mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 17.76 g of a yellow solid in 80% yield.

m/z=[M+Na] 467.1684

$^1$H NMR (600 MHz, cdc13) δ 7.64 (d, J=15.9 Hz, 1H), 7.00 (t, J=7.9 Hz, 2H), 6.76 (s, 2H), 6.51 (s, 1H), 6.39 (d, J=15.9 Hz, 1H), 6.26 (dt, J=13.8, 6.7 Hz, 1H), 4.87 (d, J=6.7 Hz, 2H), 3.90 (s, 3H), 3.88 (s, 9H), 3.87 (s, 3H), 3.84 (s, 3H).

$^{13}$C NMR (600 MHz, cdc13) δ 166.78 (s), 153.41 (s), 151.70 (s), 149.95 (s), 144.87 (s), 143.29 (s), 140.07 (s), 129.92 (s), 129.23 (s), 128.84 (s), 125.93 (s), 121.30 (s), 117.34 (s), 116.86 (s), 110.01 (s), 105.18 (s), 97.46 (s), 65.97 (s), 60.97 (s), 56.58 (s), 56.50 (s), 56.13 (s), 56.06 (s).

EXAMPLE 2

α-Asaronol Nicotinate

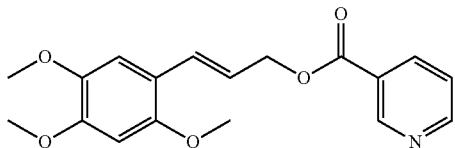 [SMILES: COc1cc(OC)c(OC)cc1/C=C/COC(=O)c1cccnc1]

Into a 100 mL single-necked flask, α-Asaronol 1.12 g (5.0 mmol), nicotinic acid 0.92 g (7.5 mmol), DMAP 0.18 g (1.5 mmol) and N,N-dimethylformamide (20 mL) were added. After stirring the mixture at room temperature for 35 minutes, EDCI 1.44 g (7.5 mmol) was added and reacted at room temperature for 8 hours. The reaction was monitored by TLC. After the completion of the reaction of raw materials, saturated sodium bicarbonate solution was added to adjust the pH to pH=7-8. The mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 0.82 g of a yellow solid in 50% yield.

EXAMPLE 3

α-Asaronol Isonicotinate

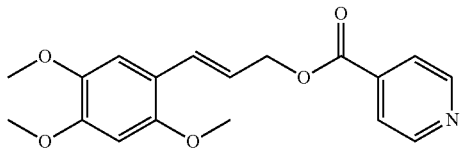 [SMILES: COc1cc(OC)c(OC)cc1/C=C/COC(=O)c1ccncc1]

Into a 100 mL single-necked flask, α-Asaronol 0.90 g (4.0 mmol), isonicotinic acid 0.74 g (6.0 mmol), DMAP 0.15 g (1.2 mmol) and trichloromethane (20 mL) were added. After stirring the mixture at room temperature for 30 minutes, EDCI 1.15 g (6.0 mmol) was added and reacted at room temperature for 6 hours. The reaction was monitored by TLC. After the completion of the reaction of raw materials, saturated sodium bicarbonate solution was added to adjust the pH to pH=7-8. The mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 0.59 g of a yellow solid in 45% yield.

EXAMPLE 4

α-Asaronol 3,4,5-trimethoxyphenylacetate

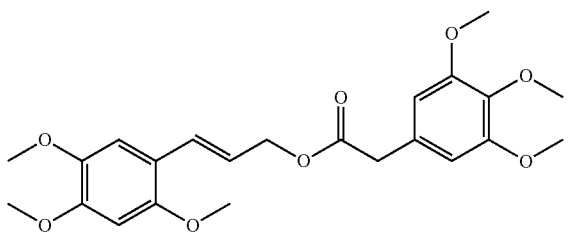

Into a 100 mL single-necked flask, α-Asaronol 1.34 g (6.0 mmol), 3,4,5-trimethoxyphenylacetic acid 2.03 g (9.0 mmol), DMAP 0.22 g (1.8 mmol) and N,N-dimethylformamide (30 mL) were added. After stirring the mixture at room temperature for 30 minutes, EDCI 1.73 g (9.0 mmol) was added and reacted at room temperature for 6 hours. The reaction was monitored by TLC. After the completion of the reaction of raw materials, saturated sodium bicarbonate solution was added to adjust the pH to pH=7-8. The mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 1.68 g of a yellow solid in 65% yield.

EXAMPLE 5

L-proline α-Asaronol ester

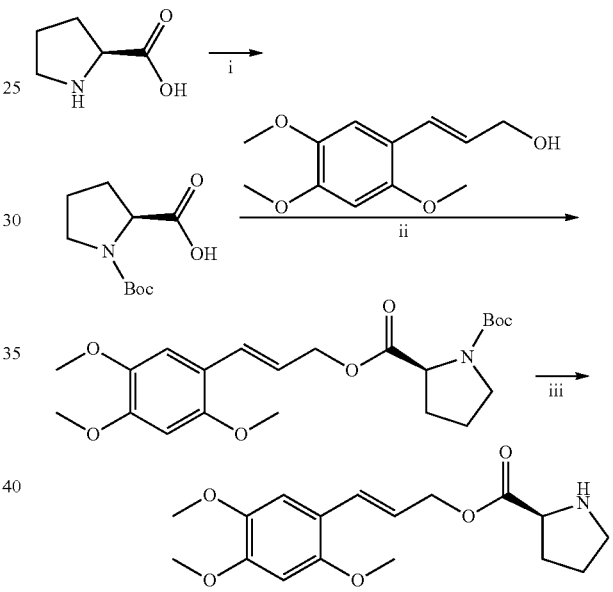

(i) Into a 100 mL three-necked flask equipped with a thermometer, L-proline 2.30 g (20.0 mmol), 1,4-dioxane (10 mL), and 2 mol/L aqueous sodium hydroxide solution (30 mL) were added. After cooling to 0° C., the mixture was stirred for 10 minutes, into which di-tert-butyl dicarbonate 6.55 g, (30.0 mmol) was added dropwise over 60 min. The mixture was slowly warmed and stirred at room temperature for 6 hours or overnight. After the pH was adjusted to pH=4 with 2 mol/L dilute hydrochloric acid, the reaction solution was extracted with ethyl acetate/water system, and washed three times. The organic phases were combined, and dried over anhydrous sodium sulfate to obtain 3.78 g of a white solid boc-L-proline in 88% yield.

(ii) Into a 100 mL single-necked flask, 1.46 g (6.8 mmol) of boc-L-proline in (i), α-Asaronol 1.01 g (4.5 mmol), DMAP 0.22 g (1.8 mmol) and dichloromethane (30 mL) were added. After stirring the mixture at room temperature for 30 minutes, EDCI 1.73 g (9.0 mmol) was added and reacted at room temperature for 6 hours. The reaction was monitored by TLC. After the completion of the reaction of raw materials, saturated sodium bicarbonate solution was added to adjust the pH to pH=7-8. The mixture was extracted and separated with ethyl acetate/water three times. The organic phases were combined, dried over anhydrous sodium sulfate, suction filtered, and concentrated under reduced pressure. The resulting crude product was isolated by silica gel column to obtain 1.10 g of a yellow solid boc-L-proline α-Asaronol in 58% yield.

(iii) Into a 100 mL single-necked flask, 0.97 g (2.3 mmol) of boc-L-proline α-Asaronol in (ii) and dichloromethane (10 mL) were added, and then trifluoroacetate (3mL) was added dropwise under nitrogen atmosphere, and the mixture was stirred at room temperature for 5 hours. After concentration under reduced pressure, ethyl acetate (20 mL), water (20 mL) and saturated aqueous sodium bicarbonate (50 mL) were added and the mixture was extracted and separated three times. The organic phases were combined, dried over anhydrous sodium sulfate, suction filtered, and concentrated under reduced pressure to obtain 0.69 g of a pale yellow solid L-proline α-Asaronol in 93% yield.

EXAMPLE 6

α-Asaronol 3,4-dihydroxy cinnamate

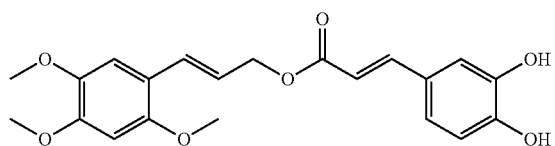 [SMILES: COc1cc(OC)c(OC)cc1/C=C/COC(=O)/C=C/c1ccc(O)c(O)c1]

Into a 100 mL single-necked flask, α-Asaronol 1.79 g (8.0 mmol), 3,4-dihydroxy cinnamic acid 2.16 g (12.0 mmol), tetrahydrofuran (30 mL), triphenylphosphine 2.10 g (8.0 mmol), and diisopropyl azodicarboxylate 1.62 g (8.0 mmol) were added at 0° C. The mixture was stirred at room temperature for 36 hours. The reaction was monitored by TLC. After the completion of the reaction of raw materials, the mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 1.24 g of a yellow solid in 40% yield.

EXAMPLE 7

α-Asaronol 3,4-dihydroxy phenylacetate

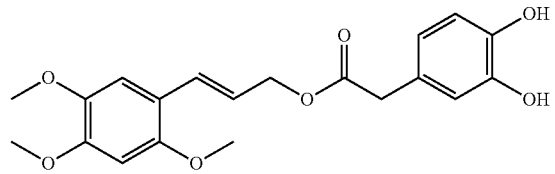 [SMILES: COc1cc(OC)c(OC)cc1/C=C/COC(=O)Cc1ccc(O)c(O)c1]

Into a 100 mL single-necked flask, α-Asaronol 1.68 g (7.5 mmol), 3,4-dihydroxy phenylacetic acid 1.90 g (11.3 mmol), tetrahydrofuran (30 mL), triphenylphosphine 1.97 g (7.5 mmol), and diisopropyl azodicarboxylate 1.52 g (7.5 mmol) were added at 0° C. The mixture was stirred at room temperature for 40 hours. The reaction was monitored by TLC. After the completion of the reaction of raw materials, the mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 1.23 g of a yellow solid in 44% yield.

EXAMPLE 8

α-Asaronol 3-nitrophenylacetate

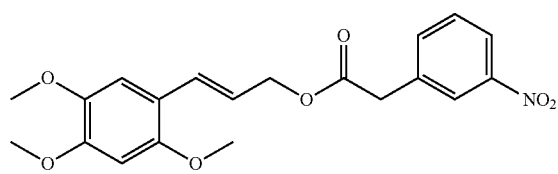 [SMILES: COc1cc(OC)c(OC)cc1/C=C/COC(=O)Cc1cccc([N+](=O)[O-])c1]

Into a 100 mL single-necked flask, α-Asaronol 0.57 g (7.0 mmol), 3-nitrophenylacetic acid 1.90 g (10.5 mmol), DMAP 0.26 g (2.1 mmol) and N,N-dimethylformamide (30 mL) were added. After stirring the mixture at room temperature for 30 minutes, EDCI 2.01 g (10.5 mmol) was added and reacted at room temperature for 6 hours. The reaction was monitored by TLC. After the completion of the reaction of raw materials, saturated sodium bicarbonate solution was added to adjust the pH to pH=7-8. The mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 0.81 g of a yellow solid in 30% yield.

EXAMPLE 9

α-Asaronol 2,5-methoxycinnamate

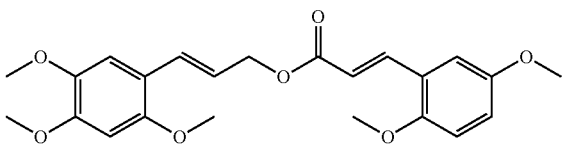

Into a 100 mL single-necked flask, α-Asaronol 0.90 g (4.0 mmol), 2,5-methoxycinnamic acid 1.25 g (6.0 mmol), DMAP 0.15 g (1.2 mmol) and dichloromethane (20 mL) were added. After stirring the mixture at room temperature for 30 minutes, EDCI 1.15 g (6.0 mmol) was added and reacted at room temperature for 9 hours. The reaction was monitored by TLC. After the completion of the reaction of raw materials, saturated sodium bicarbonate solution was added to adjust the pH to pH=7-8. The mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 1.03 g of a yellow solid in 62% yield.

EXAMPLE 10

α-Asaronol p-methoxycinnamate

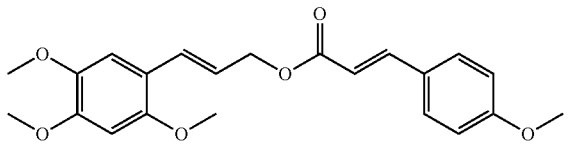

Into a 100 mL single-necked flask, α-Asaronol 0.67 g (3.0 mmol), p-methoxycinnamic acid 0.80 g (4.5 mmol), DMAP 0.11 g (0.9 mmol) and dichloromethane (20 mL) were added. After stirring the mixture at room temperature for 30 minutes, EDCI 0.86 g (4.5 mmol) was added and reacted at room temperature for 6 hours. The reaction was monitored by TLC. After the completion of the reaction of raw materials, saturated sodium bicarbonate solution was added to adjust the pH to pH=7-8. The mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 0.69 g of a yellow solid in 60% yield.

EXAMPLE 11

α-Asaronol p-chlorobenzoate

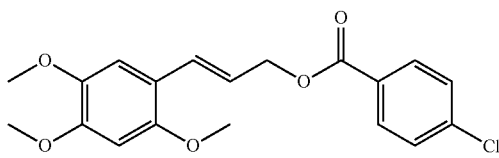 [SMILES: COc1cc(OC)c(OC)cc1/C=C/COC(=O)c1ccc(Cl)cc1]

Into a 100 mL single-necked flask, α-Asaronol 0.45 g (2.0 mmol), p-chlorobenzoic acid 0.47 g (3.0 mmol), DMAP 0.07 g (0.6 mmol) and dichloromethane (20 mL) were added. After stirring the mixture at room temperature for 30 minutes, EDCI 0.58 g (3.0 mmol) was added and reacted at room temperature for 6 hours. The reaction was monitored by TLC. After the completion of the reaction of raw materials, saturated sodium bicarbonate solution was added to adjust the pH to pH=7-8. The mixture was extracted with ethyl acetate/water system, and washed three times. The organic phases were combined, dried over anhydrous sodium sulfate, suction filtered, and concentrated under reduced pressure. The resulting crude product was isolated by silica gel column to obtain 0.35 g of a yellow solid in 48% yield.

EXAMPLE 12

α-Asaronol Propionate

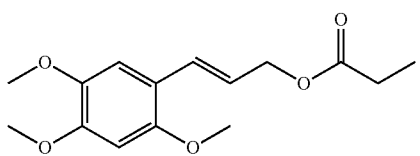 [SMILES: CCC(=O)OC/C=C/c1cc(OC)c(OC)cc1OC]

Into a 100 mL single-necked flask, propionic acid was added, and under ice bath condition, thionyl chloride (12 mL) was added. The mixture was refluxed for 3 hours, and then cooled to room temperature. After distilling off the excess of thionyl chloride under reduced pressure, tetrahydrofuran was added into the residue and stirred well, to obtain a solution of propionyl chloride in tetrahydrofuran. Under ice bath condition, α-Asaronol 0.56 g (2.5 mmol), pyridine 0.60 g (7.6 mmol) and the solution of propionyl chloride in furan were added. The mixture was stirred for 15 minutes and heated to reflux for 3 hours. After completion of the reaction, the mixture was cooled, and the pyridine hydrochloride was removed by filtration. Tetrahydrofuran was distilled off from the filtrate under reduced pressure. The residue was separated using ethyl acetate/water. The organic phases were combined, dried over anhydrous sodium sulfate, suction filtered, and concentrated under reduced pressure. The resulting crude product was isolated by silica gel column to obtain 0.44 g of a yellow solid in 65% yield.

Study on the Activity of α-Asaronol 3,4,5-trimethoxycinnamate

α-Asaronol 3,4,5-trimethoxycinnamate was used for the treatment of convulsion and epilepsy. The antiepileptic pharmacological tests were carried out using the anti-epileptic drug development program implemented by the National Institutes of Health (NIH), comprising the Maximal Electroshock Seizure (MES) for evaluating antiepileptic activity and the Rotarodtest for examining neurotoxicity. In order to further study and evaluate the pharmacological mechanism of anticonvulsant effect in different chemical models, two classic chemical model pentarotetrazole and 3-mercaptopropionic acid were used.

(1) Maximal Electroshock Seizure (MES)

MES is a common experimental model of epileptic seizures, where if the test compound is significantly against MES, the compound may be developed into a clinically effective drug for the treatment of epilepsy.

Procedure: KM mice were subjected to the following preliminary screening before they were tested, and only qualified mice were screened for the next experiment. The screening method was performed as follows: the day before the test, the test mice electrically stimulated at 15V, 60 Hz, wherein two electrodes were clamped in each ear of the mice and powered for 0.45 seconds. Mice with hind limb rigidity were included in the experimental mice and used for later experiments. The Maximal Electroshock Seizure tolerance test was performed as follows: mice were administered intragastrically with the test compound after it is dissolved, and then at 0.25 h, 0.5 h, 1 h, 2 h, 3 h and 4 h after the administration, stimulated with the electrodes in their ears at 15V, 60 Hz electric stimulation for 0.45 s, respectively. If the mice did not show hind limb rigidity, the test compound had anticonvulsant activity at the dose. According to the dosing regimen, concentration gradient was designed and the mice were administered with the test compound at different concentration gradient and observed for the anticonvulsant activity. Finally, the half effective dose of the test compound at the maximum anticonvulsant activity was calculated according to the following equation:

$$ED_{50} = 1\ g^{-1}[Xm - i(\Sigma P - 0.5)]$$

$$S_{X50} = i(\Sigma P - \Sigma P^2/n - 1)^{1/2}$$

95% confidence limit for $ED_{50} = 1\ g^{-1}(1\ gED_{50} \pm 1.96\ S_{X50})$ wherein the meanings of the symbols in the equation are as follows:

Xm common logarithm for the maximum dose;
i common logarithm for the ratio between doses
p positive rate for each group, expressed in decimal places
n the number of animals per group
$S_{X50}$ standard error of 1 $gED_{50}$

TABLE 1 result of the initial anticonvulsant test of α-Asaronol
3,4,5-trimethoxycinnamate in mice (i.g)[a]

| dose (mg/kg) | MES[b] | | | | | | $ED_{50}$[d] |
|---|---|---|---|---|---|---|---|
| | 0.25 h | 0.5 h | 1 h | 2 h | 3 h | 4 h | |
| 154 | 1/6[c] | 0 | 1/6 | 1/6 | 3/6 | 3/6 | |
| 110 | 2/6 | 1/6 | 1/6 | 2/6 | 3/6 | 3/6 | 90.3 |
| 78 | 3/6 | 3/6 | 3/6 | 3/6 | 4/6 | 4/6 | (63.1-128.8)[e] |
| 56 | 3/6 | 4/6 | 4/6 | 5/6 | 5/6 | 5/6 | |
| 40 | 4/6 | 5/6 | 6/6 | 6/6 | 6/6 | 6/6 | |

[a]the test compound plus Tween dissolved in water
[b]the Maximal Electroshock Seizure test was performed at 0.25 h, 0.5 h, 1 h, 2 h, 3 h and 4 h after intragastric administration;
[c]the number of test mice was 6;
[d]$ED_{50}$ is the half effective dose;
[e]The 95% confidence limit was given in parentheses;

(2) Neurotoxicity Test

Procedure: experimental mice were place on a rotating bar fatigue device rotating at 16 revolutions per minute at 0.25 h, 0.5 h, 1 h, and 2 h after intragastric administration, respectively. If the mice did not fall or fall within three times within three minutes, it indicates that the compound had no neurotoxicity at the dose; if the mice fall more than three times, it indicates that the compound had neurotoxicity at the dose. According to the dosing regimen, concentration gradient was designed and the mice was administered with the test compound at different concentration gradient and observed for the anticonvulsant activity. Half toxic dose ($TD_{50}$) was calculated according to the following equation:

$$TD_{50} = 1\ g^{-1}[Xm - i(\Sigma P - 0.5)]$$

$$S_{X50} = i(\Sigma P - \sigma P^2/n - 1)^{1/2}$$

95% confidence limit for TD50=1 $g^{-1}(1\ gTD_{50} \pm 1.96\ S_{X50})$
wherein the meanings of the symbols in the equation are as follows:
Xm common logarithm for the maximum dose;
i common logarithm for the ratio between doses
p positive rate for each group, expressed in decimal places
n the number of animals per group
$S_{X50}$ standard error of 1 $gTD_{50}$

TABLE 2 data analysis of the neurotoxicity and anticonvulsant
activity of α-Asaronol 3,4,5-trimethoxycinnamate (i.g)[a]

| dose (mg/kg) | Toxicity[b] | | | | $TD_{50}$[d] | $ED_{50}$[e] | PI[f] |
|---|---|---|---|---|---|---|---|
| | 0.25 h | 0.5 h | 1 h | 2 h | | | |
| 750 | 0/4[c] | 0/4 | 1/4 | 0/4 | | | |
| 825 | 0/4 | 1/4 | 1/4 | 0/4 | 939.7 | 90.3 | 10.4 |
| 900 | 2/4 | 2/4 | 2/4 | 1/4 | (706.0-1250.3)[g] | (63.1-128.8) | |
| 1000 | 3/4 | 3/4 | 2/4 | 2/4 | | | |
| 1100 | 3/4 | 4/4 | 3/4 | 3/4 | | | |
| 1200 | 3/4 | 4/4 | 4/4 | 3/4 | | | |

[a]the test compound plus Tween dissolved in water
[b]the neurotoxicity experiment was performed at 0.25 h, 0.5 h, 1 h and 2 h after intragastric administration;
[c]the number of test mice was 4;
[d]$TD_{50}$ is the half toxic dose;
[e]$ED_{50}$ is the half effective dose;
[f]PI is the protection index ($TD_{50}/ED_{50}$)
[g]The 95% confidence limit was given in parentheses Calculated by the experimental data, it is shown that α-Asaronol 3,4,5-trimethoxycinnamate exhibited $ED_{50}$=90.3 mg/kg, $TD_{50}$=939.7 mg/kg, and protection index PI=10.4 after intragastrically administered in the Maximal Electroshock Seizure test, showing good anticonvulsant activity, and did not show significant toxicity.

In order to deduce the possible anticonvulsant mechanism of α-Asaronol 3,4,5-trimethoxycinnamate, in this study, pentylenetetrazole, 3-mercaptopropionic acid and other chemical test modes were used to initially evaluate the anticonvulsant activity of the test compound (i.g: 160 mg/kg, 80 mg/kg, 40 mg/kg).

(3) Pentylenetetrazole-induced Epilepsy Experimental Model

Procedure: mice were randomly divided into five groups: treatment group (i.g: 160 mg/kg, 80 mg/kg, 40 mg/kg), control group and blank group (n=6). The treatment group was intragastrically administrated with the test compound, the control group with the positive drug carbamazepine, and the blank group with physiological saline. After 30 minutes, the mice were intragastrically administrated with pentylenetetrazole at 200 mg/kg. Each test animal was placed in one cage and observed for 60 minutes. The latency of clonic seizures, the number of clonic seizures, the number of tonic seizures, and the number of deaths for mice of each group were recorded.

TABLE 3 results of the anticonvulsant activity of α-Asaronol 3,4,5-trimethoxycinnamate
in the pentylenetetrazole-induced epilepsy mice model

| group | dose (mg/kg) | latency (s) | clonic seizures (%) | tonic seizures (%) | mortality rate (%) |
|---|---|---|---|---|---|
| α-Asaronol 3,4,5-trimethoxycinnamate | 160 | 370.0 ± 84.8* | 50 | 33.3 | 16.7 |
| | 80 | 253.6 ± 58.2* | 83.3 | 33.3 | 66.7 |
| | 40 | 205.6 ± 40.5* | 100 | 50 | 100 |
| carbamazepine | 83 | 476.8 ± 100.5** | 100 | 33.3 | 50 |
| physiological saline | — | 194.5 ± 19.8 | 100 | 100 | 100 |

**p < 0.01 vs. physiological saline group,
*p < 0.05 vs. physiological saline group In the pentylenetetrazole-induced epilepsy model, compared with the physiological saline group, α-Asaronol 3,4,5-trimethoxycinnamate at the test dose (160 mg/kg, 80 mg/kg, 40 mg/kg) can significantly prolong the time of clonic seizure in mice (p<0.05), and can inhibit the tonic seizure and reduce the mortality of mice; compared with carbamazepine, α-Asaronol 3,4,5-trimethoxycinnamate at the same dose has a comparable effect on inhibiting the tonic seizure and reducing the mortality of mice. Pentylenetetrazole incudes convulsions by inhibiting γ-aminobutyric acid (GABA) neurotransmitters, the main inhibitory neurotransmitter present in the brain and closely related to epilepsy. According table 3, α-Asaronol 3,4,5-trimethoxycinnamate perhaps inhibit or reduce pentylenetetrazol-induced seizures by increasing GABA neurotransmitters.

(4) 3-mercaptopropionic Acid-induced Epilepsy Experimental Model

Procedure: mice were randomly divided into five groups: treatment group (i.g: 160 mg/kg, 80 mg/kg, 40 mg/kg), control group and blank group (n=6). The treatment group was intragastrically administrated with the test compound, the control group with the positive drug carbamazepine, and the blank group with physiological saline. After 30 minutes, the mice were intragastrically administrated with 3-mercaptopropionic acid at 60 mg/kg. Each test animal was placed in one cage and observed for 60 minutes. The latency of the clonic seizures, the number of clonic seizures, the number of tonic seizures, and the number of deaths for mice of each group were recorded.

TABLE 4 results of the anticonvulsant activity of α-Asaronol 3,4,5-trimethoxycinnamate in the 3-mercaptopropionic acid-induced epilepsy mice model

| group | dose (mg/kg) | latency (s) | clonic seizures (%) | tonic seizures (%) | mortality rate (%) |
| --- | --- | --- | --- | --- | --- |
| α-Asaronol 3,4,5-trimethoxycinnamate | 160 | 241.5 ± 80.4* | 50 | 33.3 | 33.3 |
|  | 80 | 192.8 ± 85.1* | 83.3 | 33.3 | 33.3 |
|  | 40 | 185.3 ± 39.8 | 100 | 50 | 50 |
| carbamazepine | 83 | 277.2 ± 93.1* | 100 | 33.3 | 33.3 |
| physiological saline | — | 176.5 ± 16.7 | 100 | 100 | 100 |

*p < 0.05 vs. physiological saline group

In the 3-mercaptopropionic acid-induced epilepsy model, compared with the physiological saline group, α-Asaronol 3,4,5-trimethoxycinnamate at the test dose (160 mg/kg, 80 mg/kg) can significantly prolong the time of clonic seizure in mice (p<0.05), and can inhibit the tonic seizure and reduce the mortality of mice; compared with carbamazepine, α-Asaronol 3,4,5-trimethoxycinnamate at the test dose (160 mg/kg, 80 mg/kg) has a comparable effect on inhibiting the tonic seizure and reducing the mortality of mice. 3-mercaptopropionic acid is a competitive inhibitor of GABA synthase glutamate decarboxylase and inhibits GABA synthesis, leading to a decrease of GABA levels in brain. α-Asaronol 3,4,5-trimethoxycinnamate can moderately reduce 3-mercaptopropionic acid-induced seizures, indicating that α-Asaronol 3,4,5-trimethoxycinnamate may activate GABA synthase glutamate decarboxylase or inhibit brain GABA.

The invention claimed is:

1. Ester of α-Asaronol, having the structure of formula I

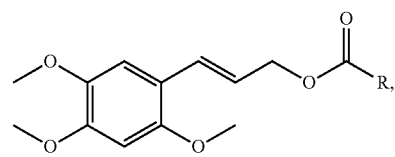

wherein,
R is selected from the group consisting of:

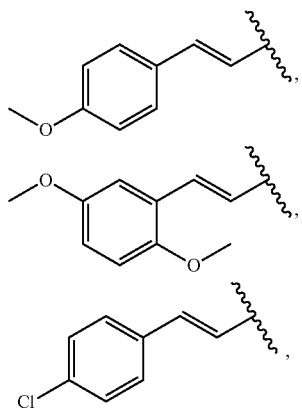

-continued

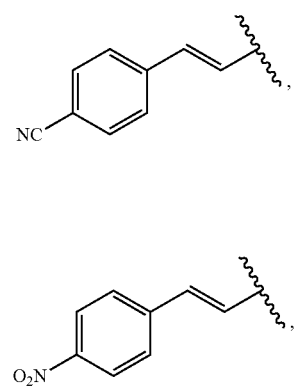

-continued
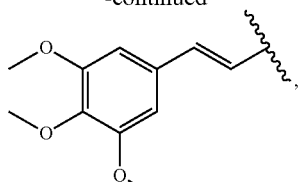,
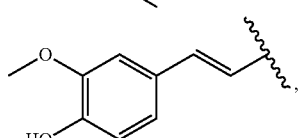,
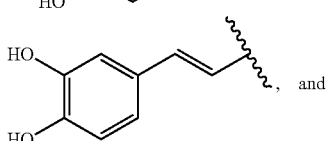, and
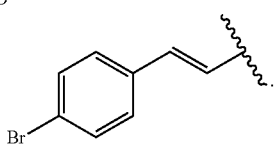.
2. A stereoisomer or a mixture of different stereoisomeric compounds of the compound of claim 1.
* * * * *